United States Patent [19]
Gilpin et al.

[11] Patent Number: 6,022,885
[45] Date of Patent: Feb. 8, 2000

[54] PYRROLIDINE AND THIAZOLE DERIVATIVES WITH ANTIBACTERIAL AND METALLO-β-LACTAMASE INHIBITORY PROPERTIES

[75] Inventors: Martin Leonard Gilpin, Dorking, United Kingdom; David John Payne, Collegeville, Pa.; John Hargreaves Bateson, Reigate, United Kingdom

[73] Assignee: SmithKline Beecham p.l.c., Brentford, United Kingdom

[21] Appl. No.: 09/029,210

[22] PCT Filed: Sep. 9, 1996

[86] PCT No.: PCT/EP96/04014

§ 371 Date: Jun. 10, 1998

§ 102(e) Date: Jun. 10, 1998

[87] PCT Pub. No.: WO97/10225

PCT Pub. Date: Mar. 20, 1997

[30] Foreign Application Priority Data

Sep. 15, 1995 [GB] United Kingdom .................. 9518920
May 24, 1996 [GB] United Kingdom .................. 9610902

[51] Int. Cl.[7] ................. A61K 31/425; A61K 31/40; C07D 207/16; C07D 277/06
[52] U.S. Cl. ................. 514/365; 514/419; 548/200; 548/571
[58] Field of Search ................. 548/200, 571; 514/365, 419

[56] References Cited

U.S. PATENT DOCUMENTS

| | | | |
|---|---|---|---|
| 4,046,889 | 9/1977 | Ondetti et al. | 424/244 |
| 4,105,776 | 8/1978 | Ondetti et al. | 424/274 |
| 4,283,407 | 8/1981 | Maten et al. | 424/270 |
| 4,307,110 | 12/1981 | Condon et al. | 424/274 |
| 4,316,906 | 2/1982 | Ondetti et al. | 424/274 |

FOREIGN PATENT DOCUMENTS

| | | |
|---|---|---|
| 868532 | 10/1978 | Belgium . |
| 0001978 | 10/1978 | European Pat. Off. . |
| 0172614 | 6/1985 | European Pat. Off. . |
| 5057561 | 10/1978 | Japan . |
| 55-009060 | 1/1980 | Japan . |
| 635087 | 3/1983 | Switzerland . |

OTHER PUBLICATIONS

J. Med. Chem. 1993 vol. 36 pp. 2390–2403, Waller et al., Three dimensional quantitative structure–activity relationship of angiotesin converting enzyme and thermolysin inhibitors.

J. Computer–Aided Molecular Design 1987, 1, pp. 133–142, A theoretical study of angiotension–converting enzyme inhibitors.

*Primary Examiner*—Floyd D. Higel
*Attorney, Agent, or Firm*—James M. Kanagy; Charles M. Kinzig

[57] ABSTRACT

This invention relates to a method of treating bacterial infections in humans or animals comprising administering, in combination with a β-lactam antibiotic, a therapeutically effective amount of a compound of formula (I).

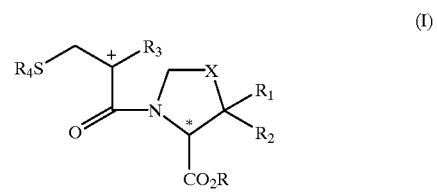

3 Claims, No Drawings

PYRROLIDINE AND THIAZOLE DERIVATIVES WITH ANTIBACTERIAL AND METALLO-β-LACTAMASE INHIBITORY PROPERTIES

This application is an application filed under the provisions of 35 U.S.C. §371of PCT application serial number PCT/EP 96/04014 filed Sep. 09, 1996.

This invention relates to chemical compounds having metallo-β-lactamase inhibitory and antibacterial properties. The invention also relates to methods for the preparation of such compounds, to pharmaceutical compositions containing them, and to uses thereof.

Metallo-β-lactamases confer resistance to the vast majority of β-lactam based therapies, including carbapenems and jeopardise the future use of all such agents. As a result of the increased use of carbapenems and other β-lactam antibiotics the clinical climate is becoming more favourable for the survival of clinical strains which produce metallo-B-lactamases, and metallo-β-lactamases have now been identified in common pathogens such as *Bacillus fragilis*, Kiebsiella, *Pseudomonas aeruginosa* and *Serratia marcescens*. Emerging knowledge emphasises that metallo-β-lactamases have the potential to present a crisis situation for antimicrobial chemotherapy. U.S. Pat. No. 4,046,889, U.S. Pat. No. 4,105,776, U.S. Pat. No. 4,307,110, U.S. Pat. No. 4,316,906, BE868532, CH635087, J55057561, J55009060, U.S. Pat. No. 4,283,407, EP0001978, Saunders et al., J. Computer-Aided Molecular Design 1987, 1, 133 and Waller et al., J. Med. Chem. 1993, 36, 2390 disclose various substituted proline and thiazolidine compounds having anti-hypertensive activity.

According to the present invention there is provided a method of treatment of bacterial infections in humans or animals which comprises administering, in combination with a β-lactam antibiotic, a therapeutically effective amount of a compound of formula (I) or a pharmaceutically acceptable salt, solvate or in vivo hydrolysable ester thereof:

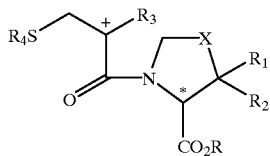

(I)

wherein:

X is S, S(O)$_n$ or CH$_2$;

n is 1 or 2

R is hydrogen, a salt forming cation or an in vivo hydrolysable ester-forming group;

R$_1$ and R$_2$ are each hydrogen or an organic substituent group;

R$_3$ is hydrogen, (C$_{1-6}$)alkyl optionally substituted by up to three halogen atoms, (C$_{2-6}$)alkenyl, (C$_{2-6}$)alkynyl, aryl, aryl(C$_{1-6}$)alkyl, heterocyclyl or heterocyclyl(C$_{1-6}$)alkyl; and R$_4$ is hydrogen, or an in vivo hydrolysable acyl group.

The compound of formula (I) may exist in a number of isomeric forms, all of which, including racemic and diastereoisomeric forms, are encompassed within the scope of the present invention.

It is preferred that the stereochemistry at the carbon atom marked * is D-, i.e. is S when X=S and is R when X=CH$_2$ and R$_1$, R$_2$=H or alkyl.

Although racemic and other mixtures of (*) D- and L-diastereomers of known compounds of formula (I) have been described, there has been little or no attempt to isolate pure D- isomers as herein defined because the antihypertensive activity of the compounds has been found to reside predominantly in the L-isomer.

R$_3$ aryl(C$_{1-6}$)alkyl includes optionally substituted benzyl, phenethyl and phenylpropyl.

Certain compounds of formula (I) including compounds where R$_3$ represents (C$_{1-6}$)alkyl substituted by up to three halogen atoms, aryl, aryl(C$_{1-6}$)alkyl, heterocyclyl or heterocyclyl(C$_{1-6}$)alkyl, hereinafter defined as R$_3^1$ and X is S are novel and as such form part of the invention. Compounds of formula (I) in which R$_3$ is R$_3^1$ and X is S are hereafter referred to as compounds of formula (IA).

Preferably R$_3$ is optionally substituted benzyl, more preferably benzyl.

The preferred stereochemistry at the carbon atom marked (+) is S.

R$_4$ is preferably hydrogen, lower alkylcarbonyl, optionally substituted benzoyl or optionally substituted phenyl lower alkyl carbonyl.

Suitable examples of R$_4$ include hydrogen and acetyl.

In general formula (I), R$_1$ and R$_2$ denotes hydrogen or an organic group. This may suitably be linked through a carbon atom. For example, R$_1$ or R$_2$ may represent hydrogen or a group of formula —R$^5$, where R$^5$ denotes an unsubstituted or substituted (C$_{1-10}$)hydrocarbon group.

Preferably, R$_1$ or R$_2$ represents hydrogen, (C$_{1-10}$)alkyl, aryl, heterocyclyl or substituted (C$_{1-10}$)alkyl, wherein the substituent may be aryl, heterocyclyl, hydroxy. (C$_{1-6}$) alkoxy, (C$_{1-6}$)alkanoyloxy, halogen, mercapto, (C$_{1-6}$) alkylthio, heterocyclylthio, amino, (mono or di)-(C$_{1-6}$) alkylamino, (C$_{1-6}$)alkanoylamino, carboxy, or (C$_{1-6}$) alkoxycarbonyl.

Examples of suitable organic groups R$_1$ and R$_2$ include methyl, ethyl, propyl, hydroxymethyl, methoxymethyl, ethoxymethyl, acetoxymethyl, (1 or 2)-acetoxyethyl, aminomethyl, 2-aminoethyl, acetamidomethyl, 2-acetamidoethyl, carboxymethyl, phenyl, pyridyl, pyrimidyl and isoxazolyl.

In particular, R$_1$ and R$_2$ may be hydrogen or methyl.

Examples of suitable optional substituents for the above-mentioned (C$_{1-6}$)alkyl, (C$_{2-6}$)alkenyl, (C$_{2-6}$)alkynyl, aryl and aryl(C$_{1-6}$)alkyl substitutents include (C$_{1-6}$)alkanoyl, (C$_{1-6}$)alkanoyloxy, heterocyclyl, amino, (C$_{1-6}$) alkanoylamino, (mono or di)-(C$_{1-6}$)alkylamino, hydroxy, (C$_{1-6}$)alkylsulphinyl, (C$_{1-6}$)alkylsulphonyl, heterocyclylthio, arylthio, sulphamoyl, carbamoyl, amidino, guanidino, nitro, halogen, carboxy, carboxy salts, carboxy esters, arylcarbonyl and heterocyclylcarbonyl groups.

X is preferably S.

Suitable pharmaceutically acceptable salts of the carboxylic acid group of the compound of formula (I) (or of other carboxylic acid groups which may be present as optional substituents) include those in which R is a metal ion e.g. aluminium salts, alkali metal salts (e.g. sodium, lithium or potassium salts), alkaline earth metal salts (e.g. calcium or magnesium salts), ammonium salts, and substituted ammonium salts, for example those with lower alkylamines (e.g. triethylamine), hydroxy-lower alkylamines (e.g. 2-hydroxyethylamine), bis-(2-hydroxyethyl)amine, tris-(2-hydroxyethyl) amine, lower-cycloalkylamines (e.g. dicyclohexyl-amine), or with procaine, dibenzylamine, N,N-dibenzyl-ethylenediamine, 1-ephenamine, N-methylmorpholine, N-ethylpiperidine, N-benzyl-β-phenethylamine, dehydroabietylamine, ethylenediamine, N,N'-bishydroabietylethylenediamine, bases of the pyridine type (e.g. pyridine, collidine and quinoline), and other amines which have been or can be used to form quaternary ammonium salts.

Pharmaceutically acceptable salts may also be acid addition salts of any amino or substituted amino group(s) that may be present as optional substituents on the compound of formula (I), or of a heterocyclic group ring nitrogen atom. Suitable salts include for example hydrochlorides, sulphates, hydrogen sulphates, acetates, phosphates etc. and other pharmaceutically acceptable salts will be apparent to those skilled in the art. Suitable addition salts are the hydrochlorides and hydrogen sulphates.

Preferred salts are sodium salts.

Examples of suitable pharmaceutically acceptable in vivo hydrolysable ester-forming groups R include those forming esters which break down readily in the human body to leave the parent acid or its salt. Suitable groups of this type include those of part formulae (i), (ii), (iii), (iv) and (v):

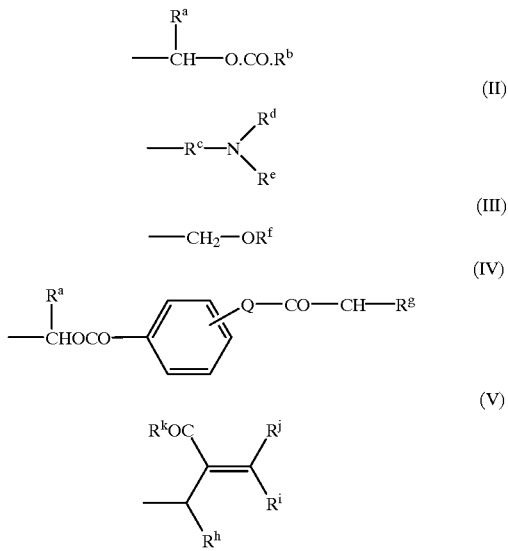

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester-forming groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl) but-2-enyl; and lactone groups such as phthalidyl and dimethoxyphthalidyl.

A further suitable pharmaceutically acceptable in vivo hydrolysable ester-forming group is that of the formula:

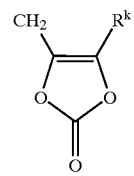

wherein $R^k$ is hydrogen, $C_{1-6}$ alkyl or phenyl.

R is preferably hydrogen.

When used herein the term 'aryl' includes phenyl and naphthyl, each optionally substituted with up to five, preferably up to three, groups selected from halogen, mercapto, $(C_{1-6})$ alkyl, phenyl, $(C_{1-6})$ alkoxy, hydroxy$(C_{1-6})$alkyl, mercapto$(C_{1-6})$alkyl, halo$(C_{1-6})$ alkyl, hydroxy, amino, nitro, carboxy, $(C_{1-6})$ alkylcarbonyloxy, alkoxycarbonyl, formyl, or $(C_{1-6})$ alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$ alkoxy, halo$(C_{1-6})$alkyl, hydroxy, carboxy, carboxy salts, carboxy esters such as $(C_{1-6})$alkoxycarbonyl, $(C_{1-6})$ alkoxycarbonyl$(C_{1-6})$alkyl, aryl, and oxo groups. Each heterocyclic ring suitably has from 4 to 7, preferably 5 or 6, ring atoms. The term 'heteroaryl' refers to heteroaromatic heterocyclic ring or ring system, suitably having 5 or 6 ring atoms in each ring. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

When used herein the terms 'lower alkyl', 'lower alkenyl', 'lower alkynyl' and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

It will be appreciated that also included within the scope of the invention are pharmaceutically acceptable salts and pharmaceutically acceptable esters, including in vivo hydrolysable esters, of any carboxy groups that may be present as optional substituents in compounds of formula (I).

Some compounds of formula (I) and (IA) may be crystallised or recrystallised from solvents such as organic solvents. In such cases solvates may be formed. This invention includes within its scope stoichiometric solvates including hydrates as well as compounds containing variable amounts of solvents such as water that may be produced by processes such as lyophilisation. Compounds of formula (I) and (IA) may be prepared in crystalline form by for example dissolution of the compound in water, preferably in the minimum quantity thereof, followed by admixing of this aqueous solution with a water miscible organic solvent such as a lower aliphatic ketone such as a di-$(C_{1-6})$ alkyl ketone, or a $(C_{1-6})$ alcohol, such as acetone or ethanol.

The compounds of formulae (I) and (IA) are metallo-β-lactamase inhibitors and are intended for use in pharmaceutical compositions. Therefore it will readily be understood that they are preferably each provided in substantially pure form, for example at least 60% pure, more suitably at least 75% pure and preferably at least 85% pure, especially at least 95% pure particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or (IA) or salt thereof.

Compounds of formula (I) may generally be prepared by processes analogous to those described in the prior art references listed above.

The present invention also provides a process for the preparation of a compound of formula (IA) as defined above, which comprises reacting a compound of formula (II)

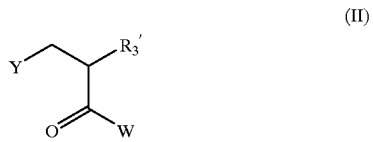

with a compound of formula (III)

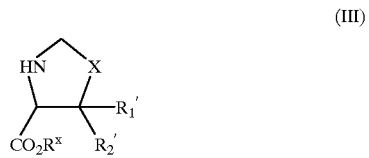

wherein W is a leaving group, Y is $R_4'S$ or a group convertible thereto, $R^x$ is R or a carboxylate protecting group and $R_1'$, $R_2'$, $R_3'$ and $R_4'$ are $R_1$, $R_2$, $R_3$ and $R_4$ or groups convertible thereto, wherein R, $R_1$, $R_2$, $R_3$ and $R_4$ are as defined in formula (IA), and thereafter, where necessary, converting Y into $R_4'S$, $R^x$, $R_1'$, $R_2'$, $R_3'$ and/or into R, $R_1$, $R_2$, $R_3$ and/or $R_4$ and optionally inter-converting R, $R_1$, $R_2$, $R_3$ and/or $R_4$.

Suitable ester-forming carboxyl-protecting groups $R^x$ other than in vivo hydrolysable ester forming groups are those which may be removed under conventional conditions. Such groups for $R^x$ include methyl, ethyl, benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus- containing group or an oxime radical of formula —N=$CHR^6$ where $R^6$ is aryl or heterocyclyl, or an in vivo hydrolysable ester radical such as defined below.

Certain compounds of formulae (II) and (III) may include an amino group which may be protected. Suitable amino protecting groups are those well known in the art which may be removed under conventional conditions if required without disruption of the remainder of the molecule.

Examples of amino protecting groups include $(C_{1-6})$ alkanoyl; benzoyl; benzyl optionally substituted in the phenyl ring by one or two substituents selected from $(C_{1-4})$ alkyl, $(C_{1-4})$ alkoxy, trifluoromethyl, halogen, or nitro; $(C_{1-4})$ alkoxycarbonyl; benzyloxycarbonyl or trityl substituted as for benzyl above; allyloxycarbonyl, trichloroethoxycarbonyl or chloroacetyl.

The compound of formula (III) is preferably presented as the anion prepared by treatment of the amine with an organic base such as triethylamine, pyridine or morpholine.

The reaction of the compounds of formula (II) and (III) is preferably carried out at ambient temperature, for example 15–25° C., in an inert solvent such as tetrahydrofuran, dichloromethane, dioxan or dimethylformamide.

Suitable examples of the leaving W group include halo such as chloro and mixed sulphonic anhydrides such as those where W is methanesulphonyloxy, toluene-p-sulphonyloxy or trifluoromethanesulphonyloxy in mixed sulphonic anhydrides.

Examples of Y convertible into $R_4'S$ include halo such as bromo which may be displaced by thiobenzoic acid or thioacteic acid.

Examples of groups $R_1'$, $R_2'$, $R_3'$, $R_4'$ convertible to $R_1$, $R_2$, $R_3$ and $R_4$ include those where any carboxy or amino group is protected by carboxy or amino protecting groups.

$R_4'$ in the compound of formula (II) is preferably other than hydrogen, for example acetyl.

The acid derivative of formula (II) is preferably prepared from the corresponding free acid by treatment with strong base such as sodium hydride followed by a source of the anion leaving group W, such as oxalyl chloride The product of the reaction of compounds of formulae (II) and (III) is a compound of formula (IV):

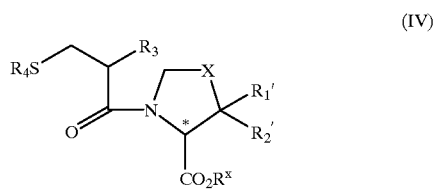

wherein the variables are as defined in formulae (II) and (III). Novel intermediates of formula (IV) wherein $R^x$ is other than R when $R_1'$, $R_2'$, $R_3'$, and $R_4'$ are $R_1$, $R_2$, $R_3$ and $R_4$ also form part of the invention.

When $R^x$ is other than hydrogen, the carboxy group —$COOR^x$ may be deprotected, that is to say, converted to a free carboxy, carboxy salt or carboxy ester group —COOR in a conventional manner, for example as described in EP0232966A.

When it is desired to obtain a free acid or salt of the preferred isomer of the formula (I) from an isomeric mixture, this may be effected by chromatographic separation of the diastereomers of the product. Where this is an ester and/or where $R_4'$ is other than hydrogen, the desired isomer may then be deprotected to give the corresponding free acid or salt. In some cases, however, it has been found particularly convenient first to deprotect the isomeric mixture to give an isomeric mixture of the free acid or salt of formula (I), followed by fractional recrystallisation to give the desired acid or salt isomer. Where X=S and the *S isomer of formula (I) is desired, it is preferred to use the corresponding *S isomer of the intermediate of formula (III).

When an enatiomerically pure form of (III) is used in the preparation of (I), the preferred diastereomer at position (+) of (I) can also be separated by chromatography. An enantiomerically pure form of (II) may also be used.

A carboxyl group may be regenerated from any of the above esters by usual methods appropriate to the particular $R^x$ group, for example, acid- and base-catalysed hydrolysis, or by enzymically-catalysed hydrolysis, or by hydrogenolysis under conditions wherein the remainder of the molecule is substantially unaffected. For example, in the case of acetonyl, by hydrolysis in acetonitrile with 0.1 M aqueous potassium hydroxide solution.

Pharmaceutically acceptable salts may be prepared from such acids by treatment with a base, after a conventional work-up if necessary. Suitable bases include sodium hydrogen carbonate to form sodium salts.

Crystalline forms of the compounds of formula (I) where R is a salt forming cation may for example be prepared by dissolving the compound (I) in the minimum quantity of water, suitably at ambient temperature, then adding a water miscible organic solvent such as a $(C_{1-6})$ alcohol or ketone such as ethanol or acetone, upon which crystallisation occurs and which may be encouraged for example by cooling or trituration.

Compounds of formulae (II) and (III) are known compounds or may be prepared by procedures analoguous to those described in the prior art references listed above.

Compounds of formula (I), particularly (IA), may be administered in the form of a pharmaceutical composition together with or a pharmaceutically acceptable carrier. The compounds of formula (I) have metallo-β-lactamase inhibitory properties, and are useful for the treatment of infections in animals, especially mammals, including humans, in particular in humans and domesticated (including farm) animals. The compounds may be used, for example, for the treatment of infections of, inter alia, the respiratory tract, the urinary tract, and soft tissues and blood, especially in humans.

The compounds may be used in combination with an antibiotic partner for the treatment of infections caused by metallo-β-lactamase producing strains, in addition to those infections which are subsumed within the antibacterial spectrum of the antibiotic partner. Metallo-β-lactamase producing strains include:- *Pseudomonas aeruginosa, Kiebsiella pneumoniae, Xanthomonas maltophilia, Bacteroides fragilis, Serratia marcescens, Bacteroides distasonis, Pseudomonas cepacia, Aeromonas hydrophila, Aeromonas sobria, Aeromonas salmonicida, Bacillus cereus, Legionella gormanii* and Flavobacterium spp.

It is generally advantageous to use a compound according to the invention in admixture or conjunction with a carbapenem, penicillin, cephalosporin or other β-lactam antibiotic and that can result in a synergistic effect, because of the metallo-β-lactamase inhibitory properties of the compounds according to the invention. In such cases, the compound of formula (I) or (IA) and the β-lactam antibiotic can be administered separately or in the form of a single composition containing both active ingredients as discussed in more detail below. The compositions of the invention include those in a form adapted for oral, topical or parenteral use and may be used for the treatment of bacterial infection in mammals including humans. The compounds of formula (I) and (IA) are particularly suitable for parenteral administration.

The compounds of formula (I) or (IA) may be formulated for administration in any convenient way for use in human or veterinary medicine, by analogy with other antibiotics and other β-lactam antibiotic/β-lactamase inhibitor combinations.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or (IA) or a pharmaceutically acceptable salt thereof is administered in the above-mentioned dosage range.

A composition according to the invention may comprise a compound of formula (I) or (IA) together with one or more additional active ingredients or therapeutic agents, for example a β-lactam antibiotic such as a carbapenem, penicillin or cephalosporin or pro-drug thereof. Carbapenems, penicillins, cephalosporins and other β-lactam antibiotics suitable for co-administration with the compound of formula (I) or (IA)—whether by separate administration or by inclusion in the compositions according to the invention—include both those known to show instability to or to be otherwise susceptible to metallo-β-lactamases and also those known to have a degree of resistance to metallo-β-lactamases.

A serine β-lactamase inhibitor such as clavulanic acid, sulbactam or tazobactam may also be co-administered with the compound of the invention and the β-lactam antibiotic, either by separate administration, or co-formulation with one, other or both of the compounds of the invention and the β-lactam antibiotic.

Examples of carbapenems that may be co-administered with the compounds according to the invention include imipenem, meropenem, biapenem, BMS181139 ([4 R-[4alpha,5beta,6beta(R*)]]-4-[2-[(aminoiminomethyl) amino]ethyl]-3-[(2-cyanoethyl)thio]-6-(1-hydroxyethyl)-7-oxo-1-azabicyclo[3.2.0]hept-2-ene-2-carboxylic acid), BO2727 ([4 R-3[3 S*,5S*(R*)],4,alpha,5beta,6beta(R*)]]-6-(1-hydroxyethyl)-3-[[5-[1-hydroxy-3-(methylamino) propyl]-3-pyrrolidinyl]thio]-4-methyl-7-oxo-1-azabicyclo [3.2.0] hept-2-ene-2-carboxylic acid monohydrochloride), ER35786 ((1 R, 5 S, 6 S)-6-[1(R)-Hydroxymethyl]-2-[2(S)-[1(R)-hydroxy-1-[pyrrolidin-3(R)-yl] methyl]pyrrolidin-4 (S)-ylsulfanyl]-1-methyl-1-carba-2-penem-3-carboxylic acid hydrochloride) and S4661 ((1 R,5 S,6 S)-2-[(3 S,5 S)-5-(sulfamoylaminomethyl) pyrrolidin-3-yl]thio-6-[(1 R)-1-hydroxyethyl]-1-methylcarbapen-2-em-3-carboxylic acid).

Examples of penicillins suitable for co-administration with the compounds according to the invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, sulbenicillin, piperacillin, and other known penicillins. The penicillins may be used in the form of pro-drugs thereof, for example as in vivo hydrolysable esters, for example the acetoxymethyl, pivaloyloxymethyl, α-ethoxycarbonyloxyethyl and phthalidyl esters of ampicillin, benzylpenicillin and amoxycillin; as aldehyde or ketone adducts of penicillins containing a 6-α-aminoacetamido side chain (for example hetacillin, metampicillin and analogous derivatives of amoxycillin); and as α-esters of carbenicillin and ticarcillin, for example the phenyl and indanyl α-esters.

Examples of cephalosporins that may be co-administered with the compounds according to the invention include, cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefuroxime, cefmetazole, cefotaxime, ceftriaxone, and other known cephalosporins, all of which may be used in the form of pro-drugs thereof.

Examples of β-lactam antibiotics other than penicillins and cephalosporins that may be co-administered with the compounds according to the invention include aztreonam, latamoxef (Moxalactam—Trade Mark), and other known β-lactam antibiotics, all of which may be used in the form of pro-drugs thereof.

Particularly suitable penicillins for co-administration with the compounds according to the invention include ampicillin, amoxycillin, carbenicillin, piperacillin, aziocillin, mezlocillin, and ticarcillin. Such penicillins may be used in the form of their pharmaceutically acceptable salts, for example their sodium salts. Alternatively, ampicillin or amoxycillin may be used in the form of fine particles of the zwitterionic form (generally as ampicillin trihydrate or amoxycillin trihydrate) for use in an injectable or infusable suspension, for example, in the manner hereinbefore described in relation to the compounds according to the invention. Amoxycillin, for example in the form of its sodium salt or the trihydrate, is particularly preferred for use in synergistic compositions according to the invention.

Particularly suitable cephalosporins for co-administration with the compounds according to the invention include cefotaxime and cefiazidime, which may be used in the form of their pharmaceutically acceptable salts, for example their sodium salts.

A compound of formula (I) or (IA) may be administered to the patient in conjunction with a β-lactam antibiotic such as a carbapenem, penicillin or cephalosporin in a synergistically effective amount.

The compounds of formula (I) or (IA) may suitably be administered to the patient at a daily dosage of from 0.7 to 50 mg/kg of body weight. For an adult human (of approximately 70 kg body weight), from 50 to 3000 mg, preferably from 100 to 1000 mg, of a compound according to the invention may be administered daily, suitably in from 1 to 6, preferably from 2 to 4, separate doses. Higher or lower dosages may, however, be used in accordance with clinical practice.

When the compositions according to the invention are presented in unit dosage form, each unit dose may suitably comprise from 25 to 1000 mg, preferably from 50 to 500 mg, of a compound according to the invention. Each unit dose may, for example. be 62.5, 100, 125, 150, 200 or 250 mg of a compound according to the invention.

When the compounds of formula (I) or (IA) are co-administered with a penicillin, cephalosporin, carbapenem or other β-lactam antibiotic, the ratio of the amount of the compound according to the invention to the amount of the other β-lactam antibiotic may vary within a wide range. The said ratio may, for example, be from 100:1 to 1:100; more particularly, it may, for example, be from 2:1 to 1:30.

The amount of carbapenem, penicillin, cephalosporin or other β-lactam antibiotic in a synergistic composition according to the invention will normally be approximately similar to the amount in which it is conventionally used per se, for example from about 50 mg, advantageously from about 62.5 mg, to about 3000 mg per unit dose, more usually about 125, 250, 500 or 1000 mg per unit dose.

The present invention further provides a compound of formula (I) or a pharmaceutically acceptable salt, solvate or or in vivo hydrolysable ester thereof, and in particular a compound of formula (IA) for use in the treatment of bacterial. infections.

The present invention also includes the use of a compound of formula (I) or a pharmaceutically acceptable salt, solvate or in vivo hydrolysable ester thereof, in the manufacture of a medicament for the treatment of bacterial infections The present invention also includes the use of a compound of formula (I) or a pharmaceutically acceptable salt, solvate or in vivo hydrolysable ester thereof as a metallo-β-lactamase inhibitor.

In a further aspect, the invention provides a method of treatment of bacterial infections in humans or animals which comprises administering, in combination with a carbapenem antibiotic, a therapeutically effective amount of a metallo-β-lactamase inhibitor.

The invention further provides the use of a carbapenem antibiotic in combination with a therapeutically effective amount of a metallo-β-lactamase inhibitor in the manufacture of a medicament for the treatment of bacterial infections.

A further composition according to the invention comprises a metallo-β-lactamase inhibitor together with a carbapenem antibiotic and a pharmaceutically acceptable carrier.

Such method and composition may be administered as described above for uses of compounds of formula (I).

All the above compositions and methods may optionally include a serine β-lactamase inhibitor as above described.

The compounds of the present invention are active against metallo-β-lactamase enzymes produced by a wide range of organisms including both Gram-negative organisms and Gram-positive organisms.

The following Examples illustrate compounds useful in the present invention, and intermediates in their preparation. (All temperatures are in ° C.).

EXAMPLES

Example 1

3-[S-acetyl-2'(RS)-benzyl-3'-mercaptopropionyl]-4(S)-carboxy-5,5-dimethylthiazolidine (E1)

To a cooled (0°), stirred solution of S-acetyl-2-benzyl-3-mercaptopropionic acid (EP0361365) (476 mg, 2.0 mmol) in dry tetrahydrofuran (8 ml) containing dry dimethylformamide (1 drop), was added sodium hydride (88 mg of a 55% suspension in oil, 2.0 mmol). The reaction mixture was allowed to reach room temperature and stirring was continued for a further 15 mins. The suspension was then recooled (0°) and treated with oxalyl chloride (210 ul, 2.4 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of 4(S)-carboxy-5,5-dimethylthiazolidine (J. Am. Chem. Soc., 1949, 71, 1137). (161 mg, 1.0 mmol) in dry tetrahydroflran (10 ml) was treated with triethylamine (278 ul, 2.0 mmol) followed by a solution of the above acid chloride in dry tetrahydrofuran (5 ml) added over 5 minutes. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material followed by the title diastereomeric mixture (1:1) as a crisp foam (312 mg, 82%). $\delta_H$ (CDCl$_3$) (Isomer 1) 1.12 (3 H, s), 1.41 (3 H, s), 2.34 (3 H, s), 2.8–3.2 (5 H, overlapping m), 3.93 (1 H, d, J 8.0 Hz), 4.35 (1 H, s), 4.61 (1 H, d, J 8.0 Hz), 7.2–7.3 (5 H, m). (Isomer 2) 1.43 (3 H, s), 1.56 (3 H, s), 2.34 (3 H, s), 2.8–3.2 (5 H, overlapping m), 4.01 (1 H, d, J 8.4 Hz), 4.55 (1 H, s), 4.59 (1 H, d, J 8.4 Hz), 7.2–7.3 (5 H, m) ppm.

Example 2

3-[2'(RS)-benzyl-3'-mereaptopropionyl]-4(S)-carboxy-5,5-dimethylthiazolidine (E2)

The S-acetyl derivative E1 (203 mg, 0.53 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title diastereomeric mixture as a crisp foam (170 mg, 94%). $\nu_{max}$ (CHCl$_3$) 1740, 1719, 1641, 1443,1425 cm$^{-1}$. $\delta_H$ (CDCl$_3$) (Isomer 1) 1.20 (3 H, s), 1.43 (3 H, s), 1.91 (1 H, dd. J 11.5 and 6.3 Hz), 2.55 (1 H, m), 2.75–3.15 (4 H, overlapping m), 4.04 (1 H, d, J 8.1 Hz), 4.38 (1 H, s), 4.84 (1 H, d, J 8.1 Hz), 7.2–7.3 (5 H, m). (Isomer 2) 1.46 (3 H, s), 1.58 (3 H, s), 2.05 (1 H, s), 2.55 (1 H, m), 2.75–3.15 (4 H, overlapping m), 4.20 (1 H, d, J 8.1 Hz), 4.62 (1 H, s), 4.81 (1 H, d, J 8.1 Hz), 7.2–7.3 (5 H, m) ppm. EIMS M$^+$339. DCIMS MH$^+$340.

Separation of diastereomers of 3-[2'(RS)-benzyl-3'-mercaptopropionyl]-4(S)-carboxy-5,5-dimethylthiazolidine by HPLC The diastereomeric mixture of Example 2 was applied to a Hypersil BDS C8 (250 mm×4.6 mm) column and eluted isocratically with 70/30 0.1% trifluoroacetic acid/0.1% trifluoroacetic acid in acetonitrile at a flow rate of 0.8 ml/minute. Detection was at 215 nm. Under these conditions the (2'R, 4 S)-diastereomer had an R$_t$ of 31.3 minutes and the (2'S, 4 S)-diastereomer had an R$_t$ of 35.1 minutes. These diastereomers were identical with the compounds E19 and E20 of Examples 19 and 20 respectively.

Example 3

N-[S-Acetyl-3'-mercapto-2'(RS)-methylpropionyl]-D-proline (E3)

To a cooled (0°), stirred solution of S-acetyl-2-methyl-3-mercaptopropionic acid (U.S. Pat. No. 4,046,889) (324 mg, 2.0 mmol) in dry tetrahydroflran (8 ml) containing dry dimethylformamide (1 drop), was added sodium hydride (88 mg of a 55% suspension in oil, 2.0 mmol). The reaction mixture was allowed to reach room temperature and stirring was continued for a further 15 mins. The suspension was then recooled (0°) and treated with oxalyl chloride (210 ul, 2.4 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of D-proline (230 mg, 2.0 mmol) in dry tetrahydrofuran (10 ml) was treated with triethylamine (556 ul, 4.0 mmol) followed by a solution of the above acid chloride in dry tetrahydrofaan (5 ml) added over 5 minutes. The mixture was stirred at ambient temperature for 18 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material followed by the title compound as a colourless oil (180 mg, 35%).

Example 4
N-[3'-Mercapto-2'(RS)-methylpropionyl]-D-proline (E4)

The S-acetyl derivative E3 (155 mg, 0.60 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound as a colourless oil (110 mg, 85%). $v_{max}$ (CHCl$_3$) 1749, 1720, 1635, 1590 cm$^{-1}$. $\delta_H$ (CDCl$_3$) (Isomer 1) 1.21 (3 H, d, J 6.8 Hz), 1.67 (1 H, dd, J 10.1 and 7.4 Hz), 2.05–2.15 (3 H, overlapping m), 2.4–2.55 (2 H, overlapping m), 2.8–3.0 (2 H, overlapping m), 3.52 (1 H, m), 3.84 (1 H, m), 4.66 (1 H, dd, J 7.7 and 2.6 Hz). (Isomer 2) 1.23 (3 H, d, J 6.8 Hz), 1.56 (1 H, dd, J 8.6 and 8.6 Hz), 2.05–2.15 (3 H, overlapping m), 2.4–2.55 (2 H, overlapping m), 2.8–3.0 (2 H, overlapping m), 3.65 (2 H, overlapping m), 4.61 (1 H, dd, J 8 and 3 Hz) ppm. EIMS M$^+$217. DCIMS MH$^+$218.

Example 5
N-(S-Acetyl-3'-mercapto-2'(S)-methylpropionyl)-D-proline (E5)

To a cooled (0°), stirred solution of S-acetyl-3-mercapto-2(S)-methylpropionic acid (Janssen Chimica, Geel, Belgium) (324 mg, 2.0 mmol) in dry tetrahydrofuran (8 ml) containing dry dimethylformamide (1 drop), was added sodium hydride (88 mg of a 55% suspension in oil, 2.0 mmol). The reaction mixture was allowed to reach room temperature and stirring was continued for a further 15 mins. The suspension was then recooled (0°) and treated with oxalyl chloride (210 ul, 2.4 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of D-proline (230 mg, 2.0 mmol) in dry tetrahydrofuran (10 ml) was treated with triethylamine (556 ul, 4.0 mmol) followed by a solution of the above acid chloride in dry tetrahydrofuran (5 ml) added over 5 minutes. The mixture was stirred at ambient temperature for 18 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material followed by the title compound as a colourless oil (119 mg, 23%). $\delta_H$ (CDCl$_3$) 1.23 (3 H, d, J 6.5 Hz), 2.0 (3 H, overlapping m), 2.34 (3 H, s), 2.45 (1 H, m), 2.92 (1 H, m), 2.96 (1 H, dd, J 13.0 and 6.5 Hz), 3.14 (1 H, dd, J 13.0 and 7.3 Hz), 3.48 (1 H, s), 3.76 (1 H, m), 4.58 (1 H, m) ppm. DCIMS MH$^+$260.

Example 6
N-(3'-mercapto-2'(S)-methylpropionyl)-D-proline (E6)

The S-acetyl derivative E5 (102 mg, 0.39 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound as a colourless oil (71 mg, 85%). $v_{max}$ (CHCl$_3$) 1751, 1719, 1636, 1586 cm$^{-1}$. $v_H$ (CDCl$_3$) 1.21 (3 H, d, J 6.7 Hz), 1.70 (1 H, dd, J 10.2 and 7.3 Hz), 2.05–2.15 (3 H, overlapping m), 2.4–2.55 (2 H, overlapping m), 2.8–3.0 (2 H, overlapping m), 3.53 (1 H, m), 3.84 (1 H, m), 4.76 (1 H, dd, J 7.8 and 3.5 Hz) ppm. EIMS M$^+$217. DCIMS MH$^+$218.

Example 7
3-[S-Acetyl-3'-mercaptopropionyl]-4(S)-carboxy-5,5-dimethylthiazolidine (E7)

To a cooled (0°), stirred solution of S-acetyl-3-mercaptopropionic acid (prepared analogously to the starting material of Example 1 according to the method of EP0361365) (148 mg, 1.0 mmol) in dry tetrahydrofuran (8 ml) containing dry dimethylformamide (1 drop), was added sodium hydride (44 mg of a 55% suspension in oil, 1.0 mmol). The reaction mixture was allowed to reach room temperature and stirring was continued for a further 15 mins. The suspension was then recooled (0°) and treated with oxalyl chloride (105 ul, 1.2 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of 4(S)-carboxy-5,5-dimethylthiazolidine (161 mg, 1.0 mmol) in dry tetrahydrofuran (10 ml) was treated with triethylamine (278 ul, 2.0 mmol) followed by a solution of the above acid chloride in dry tetrahydrofuran (5 ml) added over 5 minutes. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material followed by, on elution with 10% methanol in chloroform containing 0.1% acetic acid, the title compound as a colourless oil (70 mg, 24%). $\delta_H$ (CDCl$_3$) 1.50 (3 H, s), 1.59 (3 H, s), 2.34 (3 H, s), 2.72 (2 H, t, J 6.8 Hz), 3.14 (2 H, t, J 6.8 Hz), 4.50 (1 H, s), 4.69 (2 H, m) ppm.

Example 8
3-[3'-Mercaptopropionyl]-4(S)-carboxy-5,5-dimethylthiazolidine (E8)

The S-acetyl derivative E7 (70 mg, 0.24 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound as a colourless oil (60 mg, 100%). $v_{max}$ (CHCl$_3$) 1744, 1722, 1651, 1410 cm$^{-1}$. $\delta_H$ (CDCl$_3$) 1.52 (3 H, s), 1.60 (3 H, s), 1.81 (1 H, t, J 8.2 Hz), 2.7–2.9 (4 H, overlapping m), 4.55 (1 H, s), 4.75 (2 H, ABq) ppm. EIMS M$^+$249.0496; required for C$_9$ H$_{15}$NO$_3$S$_2$, 249.0493.

Example 9
3-[S-Acetyl-3'-mercapto-2'(S)-methylpropionyl]-4(S)-carboxy-5,5-dimethylthiazolidine (E9)

To a cooled (0°), stirred solution of S-acetyl-3-mercapto-2(S)-methylpropionic acid (162 mg, 1.0 mmol) in dry tetrahydrofuran (8 ml) containing dry dimethylformamide (1 drop), was added sodium hydride (44 mg of a 55% suspension in oil, 1.0 mmol). The reaction mixture was allowed to reach room temperature and stirring was continued for a further 15 mins. The suspension was then recooled (0°) and treated with oxalyl chloride (105 ul, 1.2 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of 4(S)-carboxy-5,5-dimethylthiazolidine (161 mg, 1.0 mmol) in dry tetrahydrofuran (10 ml) was treated with triethylamine (278 ul, 2.0 mmol) followed by a solution of the above acid chloride in dry, tetrahydrofuran (5 ml) added over 5 minutes. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material followed by, on elution with 10% methanol in chloroform containing 0.1% acetic acid, the title compound as a colourless oil (150 mg, 49%). $v_H$ (CDCl$_3$) 1.23 (3 H, d, J 6.2 Hz), 1.52 (3 H, s), 1.59 (3 H, s), 2.34 (3 H, s), 2.91 (2 H, overlapping m), 3.20 (1 H, dd, J 16.1 and 9.4 Hz), 4.53 (1 H, s), 4.71 (1 H, d, J 8.7 Hz) 4.96 (1 H, d, J 8.7 Hz) ppm.

Example 10

3-[3'-Mercapto-2'(S)-methylpropionyl]4(S)-carboxy-5,5-dimethylthiazolidine (E10)

Method A

The S-acetyl derivative E9 (150 mg, 0.49 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound as a colourless oil (129 mg, 100%). $v_{max}$ (CHCl$_3$) 1747, 1719, 1646, 1461, 1421 cm$^{-1}$. $\delta_H$ (CDCl$_3$) 1.22 (3 H, d, J 6.5 Hz), 1.52 (3 H, s), 1.61 (3 H, s), 1.87 (1 H, dd, J 11.1 and 6.7 Hz), 2.41 (1 H, dd, J 11.1 and 8.3 Hz), 2.92 (2 H, overlapping m), 4.54 (1 H, s), 4.72 (1 H, d, J 8.5 Hz), 5.01 (1 H, d, J 8.5 Hz) ppm. EIMS M$^+$263.0648; required for C$_{10}$H$_{17}$NO$_3$S$_2$, 263.0650.

Method B

The acetonyl ester E21B of Example 21 (76 mg, 0.237 mmol) in acetonitrile (4 ml) and water (1 ml) was treated with 0.1 M potassium hydroxide solution (2.4 ml, 0.237 mmol) added 0.5 ml at a time over 2 hours. After a total reaction time of 4.5 hours the reaction mixture was acidified with dilute hydrochloric acid and extracted with ethyl acetate. The organic layer was dried over magnesium sulphate and the solvent removed to afford an oil which was chromatographed on silica gel. Elution with 4% methanol in chloroform, containing 0.1% acetic acid, afforded the title compound as a gum (23 mg, 38%). The product was identical in spectroscopic properties with the compound from Method A.

Example 11

3-[S-Acetyl-2'(RS)-benzyl-3'-mercaptopropionyl]4(R)-carboxy-5,5-dimethylthiazolidine (E11)

To a cooled (0°), stirred solution of S-acetyl-2-benzyl-3-mercaptopropionic acid (238 mg, 1.0 mmol) in dry tetrahydrofuran (8 ml) containing dry dimethylformamide (1 drop), was added sodium hydride (44 mg of a 55% suspension in oil, 1.0 mmol). The reaction mixture was allowed to reach room temperature and stirring was continued for a further 15 mins. The suspension was then recooled (0°) and treated with oxalyl chloride (105 ul, 1.2 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of 4(R)-carboxy-5,5-dimethylthiazolidine (Howard-Lock etal., Can. J. Chem. 1986,64, 1215) (161 mg, 1.0 mmol) in dry tetrahydrofuran (10 ml) was treated with triethylamine (278 ul, 2.0 mmol) followed by a solution of the above acid chloride in dry tetrahydrofuran (5 ml) added over 5 minutes. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material, followed by the title compound as a crisp foam (217 mg, 57%). $v_H$ (CDCl$_3$) (Isomer 1) 1.12 (3 H, s), 1.41 (3 H, s), 2.35 (3 H, s), 2.8–3.2 (5 H, overlapping m), 3.93 (1 H, d, J 8.1 Hz), 4.36 (1 H, s), 4.61 (1 H, d, J 8.1 Hz), 7.2–7.3 (5 H, m). (Isomer 2) 1.43 (3 H, s), 1.57 (3 H, s), 2.35 (3 H, s), 2.8–3.2 (5 H, overlapping m), 4.02 (1 H d, J 8.4 Hz), 4.55 (1 H, s), 4.60 (1 H, d, J 8.4 Hz), 7.2–7.3 (5 H, m) ppm.

Example 12

3-[2'(RS)-benzyl-3'-mercaptopropionyl]-4(R)-carboxy-5,5-dimethylthiazolidine (E12)

The S-acetyl derivative E11 (217 mg, 0.57 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound, a (2'RS, 4 S) diastereomeric mixture, as a crisp foam (189 mg, 87%). $v_{max}$ (CHCl$_3$) 1739, 1720, 1643, 1432 cm$^{-1}$. $\delta_H$ (CDCl$_3$) (Isomer 1) 1.18 (3 H, s), 1.43 (3 H, s), 1.93 (1 H, dd, J 11.4 and 6.0 Hz), 2.53 (1 H, m), 2.75–3.15 (4 H, overlapping m), 4.03 (1 H, d, J 8.1 Hz), 4.37 (1 H, s), 4.84 (1 H, d, J 8.1 Hz), 7.2–7.3 (5 H, m). (Isomer 2) 1.46 (3 H, s), 1.58 (3 H, s), 2.11 (1 H, t, J 16.5 Hz), 2.53 (1 H, m), 2.75–3.15 (4 H, overlapping m), 4.19 (1 H, d, J 8.1 Hz), 4.62 (1 H, s), 4.81 (1 H, d, J 8.1 Hz), 7.2–7.3 (5 H, m) ppm. EIMS M$^+$339.0966; required for C$_{16}$H$_{21}$NO$_3$S$_2$, 339.0963.

Example 13

3-[S-Acetyl-3'-mercapto-2'RS)-methylpropionyl]-4(S)-carboxy-5,5-dimethylthiazolidine (E13)

To a cooled (0°), stirred solution of S-acetyl-3-mercapto-2(RS)-methylpropionic acid (162 mg, 1.0 mmol) in dry tetrahydrofuran (8 ml) containing dry dimethylformamide (1 drop), was added sodium hydride (44 mg of a 55% suspension in oil, 1.0 mol). The reaction mixture was allowed to reach room temperature and stirring was continued for a further 15 mins. The suspension was then recooled (0°) and treated with oxalyl chloride (105 ul, 1.2 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of 4(S)-carboxy-5,5-dimethylthiazolidine (161 mg, 1.0 mmol) in dry tetrahydrofuran (10 ml) was treated with triethylarnine (278 ul, 2.0 mmol) followed by a solution of the above acid chloride in dry tetrahydrofuran (5 ml) added over 5 minutes. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material followed by, on elution with 10% methanol in chloroform containing 0.1% acetic acid, the title compound, as a white solid (178 mg, 58%). $\delta_H$ (CDCl$_3$) 1.23 and 1.25 (3 H, d, J 6.2 Hz), 1.51 and 1.52 (3 H, s), 1.59 and 1.61 (3 H, s), 2.34 (3 H, s), 2.85–3.2 (3 H, overlapping m), 4.52 and 4.57 (1 H, s), 4.70 and 4.72 (1 H, d, J 8.6 Hz) 4.83 and 4.96 (1 H, d, J 8.6 Hz) ppm.

Example 14

3-[3'-Mercapto-2'(S)-methylpropionyl]-4(S)-carboxy-5,5-dimethylthiazolidine (E14)

The S-acetyl derivative E13 (178 mg, 0.58 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound, a (2'RS, 4 S)-diastereomeric mixture, as a colourless oil (152 mg, 99%). $v_{max}$(CHCl$_3$) 1745, 1717, 1648, 1459, 1418 cm$^{-1}$. $\delta_H$ (CDCl$_3$) 1.23 (3 H, d, J 6.4 Hz), 1.53 (3 H, s), 1.62 (3 H, s), 1.86 (1 H, dd, J 11.0 and 6.7 Hz), 2.46 (1 H, m), 2.91 (2 H, overlapping m), 4.54 and 4.64 (1 H, s), 4.73 (d, J 8.5 Hz) and 4.76 (1 H, d, J 8.3 Hz), 4.93 (d, J 8.3 Hz) and 5.02 (1 H, d, J 8.5 Hz) ppm. EIMS M$^+$263.0648; required for C$_{10}$H$_{17}$NO$_3$S$_2$, 263.0650.

Example 15

N-[S-Acetyl-2'(RS)-benzyl-3'-mercaptopropionyl]-D-proline (E15)

To a cooled (0°), stirred solution of S-acetyl-2-benzyl-3-mercaptopropionic acid (238 mg, 1.0 mmol) in dry tetrahydrofuran (8 ml) containing dry dimethylformamide (1 drop), was added sodium hydride (44 mg of a 55% suspension in oil, 1.0 mmol). The reaction mixture was allowed to reach room temperature and stirring was continued for a further 15 mins. The suspension was then recooled (0°) and treated with oxalyl chloride (105 ul, 1.2 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of D-proline (115 mg, 1.0 mmol) in dry tetrahydrofuran (10 ml) was treated with triethylamine (278 ul, 2.0 mmol) followed by a solution of the above acid chloride in dry tetrahydrofuran (5 ml) added over 5 minutes. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1 % acetic acid, afforded recovered substituted propionic acid starting material followed by the title compound as a crisp foam (87 mg, 26%). $v_H$ (CDCl$_3$) 1.50 (1 H, m), 1.85 (2 H, overlapping m), 2.35 (3 H, s), 2.50 and 2.66 (1 H, m), 2.9–3.3 (7 H, overlapping m), 4.38 and 4.57 (1 H, dd, J 8.0 and 2.0 Hz), 7.2–7.3 (5 H, m) ppm.

Example 16

N-[2'(PS)-benzyl-3'-mercaptopropionyl]-D-proline (E16)

The S-acetyl derivative E15 (87 mg, 0.26 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound, as a diastereomeric mixture, as a crisp foam (70 mg, 92%). $v_{max}$ (CHCl$_3$) 1753, 1720, 1630, 1579, 1452 cm$^{-1}$. $\delta_H$ (CDCl$_3$) 1.6 (2 H, overlapping m), 1.85 (2 H, overlapping m), 2.28 and 2.43 (1 H, m), 2.5–3.1 (6 H, overlapping m), 3.41 and 3.54 (1 H, m), 4.45 (dd, J 8.3 and 2.7 Hz) and 4.65 (1 H, dd, J 8.3 and 2.3 Hz), 7.2–7.3 (5 H, m) ppm. EIMS M$^+$293.1085; required for C$_{15}$H$_{19}$NO$_3$S, 293.1086.

Example 17

3-[S-Acetyl-2'(S)-benzyl-3'-mereaptopropionyl]-4(S)-carboxythiazolidine (E17)

To a cooled (0°), stirred solution of S-acetyl-2-benzyl-3-mercaptopropionic acid (238 mg, 1.0 mmol) in dry tetrahydrofuran (8 ml) containing dry dimethylformamide (1 drop), was added sodium hydride (44 mg of a 55% suspension in oil, 1.0 mmol). The reaction mixture was allowed to reach room temperature and stirring was continued for a further 15 mins. The suspension was then recooled (0°) and treated with oxalyl chloride (105 ul, 1.2 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of 4(S)-carboxythiazolidine (Howard-Lock et al., Can. J. Chem. 1986, 64, 1215) (133 mg, 1.0 mmol) in dry tetrahydrofaran (10 ml) was treated with triethylamine (278 ul, 2.0 mmol) followed by a solution of the above acid chloride in dry tetrahydrofuran (5 ml) added over 5 minutes. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material (120 mg, 50%) followed by the title compound as a crisp foam (103 mg, 29%). $\delta_H$(CDCl$_3$) 2.35 (3 H, s), 2.75–3.25 (7 H, overlapping m), 3.74 (d, J 8.1 Hz) and 3.86 (1 H, d, J 8.5 Hz), 4.39(d, J 8.1 Hz) and 4.55 (1 H, d, J 8.5 Hz), 4.88 (dd, J 6.7 and 2.7 Hz) and 5.04 (1 H, dd, J 6.8 and 4.0 Hz), 7.2–7.3 (5 H, m) ppm.

Example 18
3-[2'(RS)-benzyl-3'-mercaptopropionyl]-4(S)-carboxythiazolidine (E18)

The S-acetyl derivative E17 (103 mg, 0.29 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound, as a diastereomeric mixture, as a crisp foam (87 mg, 96%). $\nu_{max}$ (CHCl$_3$) 1742, 1722, 1642, 1612, 1423 cm$^{-1}$. $\delta_H$ (CDCl$_3$) 1.56 (dd, J 8.2 and 9.2 Hz) and 1.82 (1 H, dd, J 6.8 and 10.9 Hz), 2.5–3.2 (6 H, overlapping m), 3.25 (dd, J 12.0 and 3.0 Hz) and 3.36 (1 H, dd, 12.0 and 3.5 Hz), 3.87 (d, J 8.0 Hz) and 3.94 (1 H, d, J 8.3 Hz), 4.59(d, J 8.0 Hz) and 4.67 (1 H, d, J 8.3 Hz), 4.92 (dd, J 6.8 and 3.0 Hz) and 5.09 (1 H, dd, J 6.8 and 3.5 Hz), 7.2–7.3 (5 H, m) ppm. EIMS M$^+$311.0660; required for C$_{14}$H$_{17}$NO$_3$S$_2$, 311.0650.

Example 19
3-[2'(R)-benzyl-3'-mercaptopropionyl]-4(S)-carboxy-5,5-dimethylthiazolidine (E19)

A stirred solution of the carboxylic acid isomers (E1) from Example 1 (1.84 g, 4.83 mmol) in dry DMF (20 ml) was treated with potassium carbonate (0.334 g, 2.42 mmol) and chloroacetone (0.80 ml, 0.93 g, 10.0 mmol) and left to stir at room temperature overnight. The reaction mixture was then diluted with ethyl acetate and washed with 1 M hydrochloric acid followed by six water washes. The organic layer was dried over anhydrous magnesium sulphate and the solvent removed under reduced pressure to afford the acetonyl esters of compound E1 as a diastereomeric mixture (1.97 g). Chromatography on silica gel, eluting with 25% ethyl acetate/hexane, afforded the (2'R, 4 S)-isomer (E19A) as a colourless oil (0.87g, 41%). $\nu_{max}$ (CHCl$_3$) 1757, 1734, 1687, 1645, 1417cm$^1$. $\delta_H$ (CDCl$_3$) 1.47 (3 H, s), 1.61 (3 H, s), 2.18 (3 H, s), 2.34 (3 H, s), 2.85–3.15 (5 H, overlapping m), 4.02 (1 H, d, J 8.6 Hz), 4.55 (1 H, s), 4.60 (1 H, d, J 8.6 Hz), 4.62 (1 H, d, J 16.8 Hz), 4.74 (1 H, d, J 16.8 Hz), 7.25 (5 H, m) ppm. EIMS M$^+$437.1337; required for C$_{21}$H$_{27}$NO$_5$S$_2$, 437.1331. Continued elution afforded the (2'S, 4 S)-isomer (E19B) as an oil (0.98 g, 46%). $\nu_{max}$ (CHCl$_3$) 1757,1734, 1687, 1645, 1417 cm$^{31\ 1}$. $\delta_H$ (CDCl$_3$) 1.17 (3 H, s), 1.44 (3 H, s), 2.19 (3 H, s), 2.36 (3 H, s), 2.85–3.15 (5 H, overlapping m), 3.93 (1 H, d, J 8.1 Hz), 4.38 (1 H, s), 4.60 (1 H, d, J 8.1 Hz), 4.65 (1 H, d, J 16.8 Hz), 4.74 (1 H, d, J 16.8 Hz), 7.25 (5 H, m) ppm. EIMS M$^+$437.1337; required for C$_{21}$H$_{27}$NO$_5$S$_2$, 437.1331.

The acetonyl ester E19A (72 mg, 0.165 mmol) was dissolved in acetonitrile (4 ml) and treated with water (1 ml) and 0.1 M potassium hydroxide solution (3.30 ml, 0.330 mmol) and stirred at room temperature for 5 hours. The reaction mixture was then acidified with dilute hydrochloric acid and partitioned between ethyl acetate and brine. The organic layer was washed with further brine and dried over anhydrous magnesium sulphate. Removal of the solvent afforded an oil which was chromatographed on silica gel. Elution with 10% methanol/chloroform, containing 0.1% acetic acid, afforded the desired product which was contaminated with a little S-acetyl compound from incomplete hydrolysis. This product was treated with water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound as a colourless oil (40 mg, 73%). $\nu_{max}$ (CHCl$_3$) 1751, 1722, 1643, 1418 cm$^{-1}$. $\delta_H$(CDCl$_3$) 1.48 (3 H, s), 1.60 (3 H, s), about 1.6 (1 H, m, obscured), 2.59 (1 H, m), 2.75–3.15 (4 H, overlapping m), 4.21 (1 H, d, J 8.0 Hz), 4.64 (1 H, s), 4.82 (1 H, d, J 8.0 Hz), 7.2–7.3 (5 H, m) ppm. EIMS M$^+$339. DCIMS MH$^+$340.

Example 20
3-[2'(S)-benzyl-3'-mercaptopropionyl]-4(S)-carboxy-5,5-dimethylthiazolidine (E20)

The acetonyl ester E19B (0.82 g, 1.88mmol) of Example 19 in acetonitrile (40 ml) was treated with 0.1 M aqueous potassium hydroxide solution (37.6 ml, 3.76 mmol) and stirred at room temperature for 5.5 hours. Work-up and purification were as for the (R)—isomer above. Chromatography afforded the title compound as a crisp foam (372 mg, 58%). $\nu_{max}$ (CHCl$_3$) 1749, 1720, 1640, 1421 cm$^{-1}$. $\delta_H$ (CDCl$_3$) 1.18 (3 H, s), 1.43 (3 H, s), 1.94 (1 H, dd, J 11.8 and 6.2 Hz), 2.50 (1 H, ddd, J 11.8, 11.8, 2.4 Hz), 2.88 (2 H, overlapping m), 3.12 (2 H, overlapping m), 4.03 (1 H, d, J 8.1 Hz), 4.38 (1 H, s), 4.85 (1 H, d, J 8.1 Hz), 7.2–7.3 (5 H, m) ppm. EIMS M$^+$339. DCIMS MH$^+$340.

Example 21
3-[3'-Mercapto-2'(R)-methylpropionyl]-4(S)-carboxy-5,5-dimethylthiazolidine (E21)

A stirred solution of the S-acetyl derivative E13 obtained in Example 13 (450 mg, 1.47 mmol) in dry DMF (5 ml) was treated with potassium carbonate (102 mg, 0.738 mmol) and chloroacetone (0.235 ml, 273 mg, 2.95 mmol) and the mixture stirred overnight at room temperature. The reaction mixture was then diluted with ethyl acetate and washed with 1 M hydrochloric acid followed by six water washes. The organic layer was dried over anhydrous magnesium sulphate and the solvent removed under reduced pressure to afford the acetonyl esters of compound E13 as a diastereomeric mixture (0.53 g).

The acetonyl ester mixture (388 mg, 1.07 mmol) was then dissolved in acetonitrile (2 ml) containing concentrated ammonia solution (0.8 ml, sp. gr. 0.88) and water (1.2 ml) and stirred for 1 hour. The reaction mixture was acidified with 5 M hydrochloric acid solution and extracted with ethyl acetate. The organic layer was washed with water and saturated brine, dried over magnesium sulphate, and the solvent removed to afford an oil which was chromatographed on silica gel. Elution with ethyl acetate/hexane (1:2) gave the (2'S, 4 S)-isomer E21B (56 mg, 16%). $\nu_{max}$ (CHCl$_3$) 1756, 1736, 1648, 1459, 1417 cm$^{-1}$. $\delta_H$ (CDCl$_3$) 1.20 (3 H, d, J 6.4 Hz), 1.56 (3 H, s), 1.64 (3 H, s), 1.81 (1 H, dd, J 10.9 and 6.6 Hz), 2.18 (3 H, s), 2.41 (1 H, dd, J 10.9 and 8.4 Hz), 2.90 (2 H, overlapping m), 4.55 (1 H, s), 4.62 (1 H, d, J 16.8 Hz), 4.71 (1 H, d, J 8.7 Hz), 4.85 (d, J 16.8 Hz) and 5.00 (1 H, d, J 8.7 Hz) ppm. EIMS M$^+$319.0909; required for C$_{13}$H$_{21}$NO$_4$S$_2$, 319.0912. Continued elution gave the (2'R, 4 S)-isomer E21A (65 mg, 19%). $\nu_{max}$ (CHCl$_3$) 1756, 1737, 1648, 1461, 1417 cm$^{-1}$. $\delta_H$ (CDCl$_3$) 1.20 (3 H, d, J 6.4 Hz), 1.55 (3 H, s), 1.55 (1 H, m), 1.64 (3 H, s), 2. 17 (3 H, s), 2.47 (1 H, dd, J 9.5 and 8.4 Hz), 2.90 (2 H, overlapping m), 4.61 ( 1 H, d, J 16.8 Hz), 4.64 (1 H, s), 4.76 (1 H, d, J 8.3 Hz), 4.81 (d, J 16.8 Hz) and 4.91 (1 H, d, J 8.3 Hz). ppm. EIMS M$^+$319.0909; required for C$_{13}$H$_{21}$NO$_4$S$_2$, 319.0912.

The acetonyl ester E21A (87 mg, 0.273 mmol) in acetonitrile (4 ml) and water (1 ml) was treated with 0.1 M potassium hydroxide solution (2.7 ml, 0.27 mmol) added 0.5 ml at a time over 2 hours. After a total reaction time of 6 hours the reaction mixture was acidified with dilute hydrochloric acid and extracted with ethyl acetate. The organic layer was dried over magnesium sulphate and the solvent removed to afford an oil which was chromatographed on silica gel. Elution with 4% methanol in chloroform, containing 0.1% acetic acid, afforded the title compound as a gum (34 mg, 47%). $v_{max}$ (CHCl$_3$) 1752, 1719, 1647, 1457, 1419 cm$^{-1}$. $\delta_H$ (CDCl$_3$) 1.21 (3 H, d, J 6.3 Hz), 1.51 (3 H, s), 1.51 (1 H, obscured), 1.60 (3 H, s), 2.47 (1 H, dd, J 9.3 and 8.5 Hz), 2.92 (2 H, overlapping m), 4.61 (1 H, s), 4.75 (1 H, d, J 8.3 Hz), 4.91 (1 H, d, J 8.3 Hz) ppm. EIMS M$^+$263.0648; required for C$_{10}$H$_{17}$NO$_3$S$_2$, 263.0650.

Example 22

3-[S-Acetyl-3'-mercapto-2'(S)-methylpropionyl]-4(R)-carboxy-5,5-dimethylthiazolidine (E22)

To a cooled (0°), stirred solution of S-acetyl-3-mercapto-2(S)-methylpropionic acid (1 62 mg, 1.0 mmol) in dry tetrahydroflran (8 ml) containing dry dimethylformamide (1 drop), was added sodium hydride (44 mg of a 55% suspension in oil, 1.0 mmol). The reaction mixture was allowed to reach room temperature and stirring was continued for a further 15 mins. The suspension was then recooled (0°) and treated with oxalyl chloride (105 ul, 1.2 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of 4(R)-carboxy-5,5-dimethylthiazolidine (161 mg, 1.0 mmol) in dry tetrahydrofuran (10 ml) was treated with triethylamnine (278 ul, 2.0 mmol) followed by a solution of the above acid chloride in dry tetrahydrofuran (5 ml) added over 5 minutes. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material followed by, on elution with 10% methanol in chloroform containing 0.1% acetic acid, the title compound as a colourless oil (164 mg, 54%). $\delta_H$ (CDCl$_3$) 1.24 (3 H, d, J 6.4 Hz), 1.51 (3 H, s), 1.61 (3 H, s), 2.34 (3 H, s), 2.95 (2 H, overlapping m), 3.10 (1 H, dd, J 13.0 and 7.6 Hz), 4.56 (1 H, s), 4.72 (1 H, d, J 8.5 Hz) 4.83 (1 H, d, J 8.5 Hz) ppm.

Example 23

3-[Mercapto-2'(S)-methylpropionyl]-4(R)-carboxy-5,5-dimethylthiazolidine (E23)

The S-acetyl derivative E22 (164 mg, 0.54 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound as a colourless oil (139 mg, 100%). $v_{max}$ (CHCl$_3$) 1748, 1720,1650, 1459,1421 cm$^{-1}$. $\delta_H$ (CDCl$_3$) 1.23 (3 H, d, J 6.4 Hz), 1.53 (3 H, s), 1.53 (1 H, obscured), 1.61 (3 H, s), 2.49 (1 H, dd, J 9.5 and 8.5 Hz), 2.88 (2 H, overlapping m), 4.63 (1 H, s), 4.75 (1 H, d, J 8.3 Hz), 4.92 (1 H, d, J 8.3 Hz) ppm. EIMS M$^+$263.0648; required for C$_{10}$H$_{17}$NO$_3$S$_2$, 263.0650.

Example 24

N-[S-Acetyl-2'(RS)-benzyl-3'-mereaptopropionyl]-L-prolne (E24)

To a cooled (0°), stirred solution of S-acetyl-2-benzyl-3-mercaptopropionic acid (238 mg, 1.0 mmol) in dry tetrahydrofuran (8 ml) containing dry dimethylformamide (1 drop), was added sodium hydride (44 mg of a 55% suspension in oil, 1.0 mmol). The reaction mixture was allowed to reach room temperature and stirring was continued for a further 15 mins. The suspension was then recooled (0°) and treated with oxalyl chloride (105 ul, 1.2 mmol) and stirred at room ambient temperature for 30 mins. The resulting mixture was then evaporated in vacuo and the residue suspended in dry tetrahydrofuran (5 ml). The filtered solution was taken to dryness once more to afford the acid chloride as an oil.

A stirred, cooled (0°) suspension of L-proline (115 mg, 1.0 mmol) in dry tetrahydrofuran (10 ml) was treated with triethylamine (278 ul, 2.0 mmol) followed by a solution of the above acid chloride in dry tetrahydrofuran (5 ml) added over 5 minutes. The mixture was stirred at ambient temperature for 3 hours and then partitioned between ethyl acetate and 1 M hydrochloric acid. The organic layer was washed with water and saturated brine and dried over anhydrous sodium sulphate. Evaporation of the solvent afforded crude product as an oil which was chromatographed on silica gel. Elution with 4% methanol in chloroform, containing 0.1% acetic acid, afforded recovered substituted propionic acid starting material followed by the title compound as a crisp foam (80 mg, 24%). $\delta_H$ (CDCl$_3$) 1.50 (1 H, m), 1.85 (2 H, overlapping m), 2.35 (3 H, s), 2.50 and 2.66 (1 H, m), 2.9–3.3 (7 H, overlapping m), 4.38 and 4.57 (1 H, dd, J 8.0 and 2.0 Hz), 7.2–7.3 (5 H, m) ppm.

Example 25

N-[2'(RS)-benzyl-3'-mercaptopropionyl]-L-proline (E25)

The S-acetyl derivative E24 (80 mg, 0.24 mmol) was dissolved in water (0.6 ml) and concentrated aqueous ammonia (0.4 ml, sp.gr. 0.88) and stirred at room temperature for 1 hour. The reaction mixture was diluted in ethyl acetate and washed with sufficient dilute hydrochloric acid to acidify the aqueous phase. The two-phase system was treated with saturated brine and the organic layer separated, washed with further brine, dried over sodium sulphate and evaporated to afford the title compound as a crisp foam (70 mg, 100%). $v_{max}$ (CHCl$_3$) 1749, 1716, 1633, 1583, 1450 cm$^{-1}$. $\delta_H$ (CDCl$_3$) 1.6 (2 H, overlapping m), 1.85 (2 H, overlapping m), 2.28 and 2.43 (1 H, m), 2.5–3.1 (6 H, overlapping m), 3.41 and 3.54 (1 H, m), 4.45 (dd, J 8.3 and 2.7 Hz) and 4.65 (1 H, dd, J 8.3 and 2.3 Hz), 7.2–7.3 (5 H, m) ppm. EIMS M$^+$293.1085; required for C$_{15}$H$_{19}$NO$_3$S, 293.1086.

Example 26

3-[2'(S)-benzyl-3'-mercaptopropionyl]-4(S)-carboxy-5,5-dimethylthiazolidine-1-oxide (E26) (sulphoxide isomer A)

A stirred solution of the S-acetyl acetonyl ester E19B (42 mg, 0.096 mmol, prepared as in Example 19) in dichloromethane (3 ml) was treated with m-chloroperbenzoic acid (21 mg, 0.096 mmol) and stirred for a further 1 hour at ambient temperature. The reaction mixture was then washed with saturated sodium bicarbonate solution, dried over magnesium sulphate, and the solvent removed to afford crude product which was chromatographed on silica gel. Elution with ethyl acetate/hexane (1:1) gave sulphoxide isomer A (32 mg, 72%). $v_{max}$ (CHCl$_3$) 1758, 1734, 1685, 1656, 1413, 1063 cm$^{-1}$. $\delta_H$ (CDCl$_3$) 1.33 (3 H, s), 1.56 (3 H, s), 2.19 (3 H, s), 2.35 (3 H, s), 2.85–3.15 (5 H, overlapping m), 4.08 (1 H, d, J 11.9 Hz), 4.59 (1 H, d, J 16.8 Hz), 4.69 (1 H, d, J 11.9

Hz), 4.73 (1 H, s), 5.04 (1 H, d, J 16.8 Hz), 7.25 (5 H, m) ppm. APCI-MS MNH$_4^+$471. Continued elution gave sulphoxide isomer B (12 mg, 28%). $v_{max}$ (CHCl$_3$) 1762, 1734, 1685, 1656, 1417, 1063 cm$^{-1}$. $\delta_H$(CDCl$_3$) 0.95 (3 H, s), 1.42 (3 H, s), 2.19 (3 H, s), 2.37 (3 H, s), 2.85–3.15 (5 H, overlapping m), 4.14 (1 H, d, J 11.2 Hz), 4.25 (1 H, d, J 11.2 Hz), 4.58 (1 H, s), 4.62 (1 H, d, J 16.8 Hz), 4.79 (1 H, d, J 16.8 Hz), 7.25 (5 H, m) ppm. APCI-MS MNH4$^+$471.

The sulphoxide isomer A (31 mg, 0.068mmol) in acetonitrile (1.5 ml) was treated with 0.1 M potassium hydroxide (1.37 ml, 0.137mmol) and stirred at room temperature for 4 hours. The reaction mixture was diluted with ethyl acetate and acidified with dilute hydrochloric acid. The organic layer was washed with water and saturated brine and dried over magnesium sulphate. Removal of the solvent afforded an oil which was treated with concentrated ammonia solution (0.4 ml) and water (0.6 ml) and stirred for 1 hour. A repeat of the above work-up gave the crude product. Chromatography afforded the title compound as a crisp foam (12 mg, 49%). $v_{max}$ (CHCl$_3$) 1631 cm$^{-1}$. $\delta_H$ (CDCl$_3$+few drops MeOD) 1.25 (3 H, s), 1.29 (3 H, s), 1.95 (1 H, s), 2.43 (1 H, d, J 11.4 Hz), 2.8–3.1 (4 H, overlapping m), 4.02 (1 H, d, J 11.0 Hz), 4.38 (1 H, s), 4.91 (1 H, d, J 11.0 Hz), 7.2–7.3 (5 H, m) ppm. ESMS MH$^+$356.

Example 27
3-[2'(S)-benzyl-3'-mercaptopropionyl]-4(S)-carboxy-5,5-dimethylthiazolidine-1-oxide (sulphoxide isomer B) (E27)

The title compound was prepared by procedures generally described herein.

Example 28
3-[2'(S)-benzyl-3'-mercaptopropionyl]-4(R)-carboxy-5,5-dimethylthiazolidine (E28)

The title compound was prepared from E11 using methods outlined in Examples 19 and 20. NMR identical to E19.

Example 29
3-[2'(R)-benzyl-3'-mercaptopropionyl]-4(R)-carboxy-5,5-dimethylthiazolidine (E29)

The title compound was prepared from E11 using methods outlined in Example 19. NMR identical to E20.

Example 30
3-[2'(R or S)-benzyl-3'-mercaptopropionyl]-4(S)-carboxythiazolidine (E30)

The title compound was prepared from E17 using methods outlined in Examples 19 and 20. EIMS M$^+$311.0654, calculated for C$_{14}$H$_{17}$NO$_3$S$_2$ 311.0650.

Example 31
3-[2'(S or R)-benzyl-3'-mercaptopropionyl]-4(S)-carboxythiazolidine (E31)

The title compound was prepared from E17 using methods outlined in Examples 19 and 20. EIMS M$^+$311.0650, calculated for C$_{14}$H$_{17}$NO$_3$S$_2$ 311.0650.

Example 32
3-[2'(RS)-mercaptomethyl-4'-phenylbutanoyl]-4(S)-carboxy-5,5-dimethylthiazolidine (E32)

a) 2-Acetylthiomethyl-4-phenylbutanoic acid

A mixture of 2-phenylethylmalonic acid (1.8 g), 40% aqueous dimethylamine (1.08 ml, 1 eq) and 37% aqueous formaldehyde (0.64 ml, 1 eq) in water (10 ml) was stirred at room temperature overnight. After cooling at 0° C. the solid was filtered off, washed with water and dried. The white solid was heated at 170° C. for 10 minutes and cooled to room temperature. The resulting gum was dissolved in ethyl acetate (20 ml), washed with 10% potassium hydrogen sulphate solution (10 ml), water (2×10 ml), saturated brine (10 ml), dried (MgSO$_4$) and evaporated to give crude 2-methylene4-phenylbutanoic acid. $\delta_H$(CDCl$_3$) 2.55–2.90 (4 H, m, 2×CH$_2$), 5.65, 6.85 (2 H, 2×s,

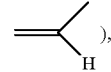

7.25 (5 H, m, Ph). The solid was dissolved in thioacetic acid (1 ml) and heated at 100° C. for 1 hour. After evaporation the gum was dissolved in ethyl acetate (10 ml) and extracted with saturated sodium hydrogen carbonate solution (2×10 ml). The combined extracts were washed with ethyl acetate (2×10 ml) and acidified with 10% potassium hydrogen sulphate solution (pH 3). The aqueous layer was extracted with ethyl acetate (2×10 ml) and the combined extracts washed with water (2×10 ml), dried (MgSO$_4$) and evaporated to yield the title compound as a yellow oil (0.52 g, 24%); $\delta_H$(CDCl$_3$) 2.00 (2 H, m, CH$_2$), 2.71 (3 H, m, CH$_2$, CH), 3.14 (2 H, m, CH$_2$), 7.24 (5 H, m, Ph). EIMS M$^+$252 DCIMS MNH$_4^+$270.

b) 3-[2'(RS)-mercaptomethyl-4'-phenylbutanoyl]-4(S)-carboxy-5,5-dimethylthiazolidine The title compound was prepared from 2-acetylthiomethyl-4-phenylbutanoic acid using methods outlined in Examples 17 and 18. EIMS M$^+$353, ESMS M-H 352.

Example 33
3-[2'(RS)-mercaptomethyl-5'-phenylpentanoyl]-4(S)-carboxythiazolidine (E33)

a) 2-Acetylthiomethyl-5-phenylpentanoic acid

3-Phenylpropylialonic acid (6.14 g) was converted to 2-methylene-5-phenylpentanoic acid (2.1 g, 40%) by the method described in Example 32a). $\delta_H$(CDCl$_3$) 1.88 (2 H, m, CH$_2$), 2.37 (2 H, t, J 7.6 Hz, CH$_2$), 2.67 (2 H, t, J 7.6 Hz, CH$_2$), 5.68 and 6.33 (2 H, 2×s,

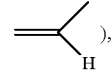

7.26 (5 H, m, Ph). The solid was dissolved in thioacetic acid (5 ml) and heated at 100° C. for 2 hours. Evaporated to give the title compound (2.9 g, 100%); $\delta_H$(CDCl$_3$) 1.71 (4 H, m, 2×CH$_2$), 2.33 (3 H, s, COCH$_3$), 2.64 (3 H, m, CH, CH$_2$), 3.08 (2 H, m, CH$_2$), 7.27 (5 H, m, Ph).

b) 3-[2'(RS)-mercaptomethyl-5'-phenylpentanoyl]-4(S)-carboxythiazolidine

The title compound was prepared from 2-acetylthiomethyl-5-phenylpentanoic acid using methods outlined in Examples 17 and 18. EIMS M$^+$339.0966, calculated for C$_{16}$H$_{21}$NO$_3$S$_2$ 339.0963.

The following compounds are described in the literature as ACE inhibitors:

| | |
|---|---|
| E4 | Saunders et al., J. Computer-Aided Molecular Design 1987, 1, 133 |
| E6 | Waller et al., J Med Cem 1993 36 (16) 2390 |
| E8 | JP55009060 |
| E14 | JP55009060 |
| E24, E25 | US4046889 |

BIOLOGICAL ACTIVITY $I_{50}$ screen

The inhibitory activity of the compounds of the invention was measured in 25 mM PIPES pH 7 buffer at 10 concentrations (1000, 333, 111, 37, 12.3, 4.1, 1.4 0.46, 0.15 and 0.05 μM) at 37° C. using nitrocefin (91 μM, final concentration) as the reporter substrate. The assays were performed with a 5 minute preincubation of enzyme and inhibitor and were conducted in the presence of added zinc sulphate ($Zn^{2+}$100 μM, final concentration). The methodology is described in detail in the following references: Payne et al (1991), *J. Antimicrob. Chemother.*, 28:255; Payne et al (1994), *Antimicrob. Agents and Chemother.*, 38:767.

Results

Compounds of the Examples 2, 4, 6, 8, 10, 12, 14, 16, 18, 20, 23, 25, 26, 28, 29, 30, 31, 32 and 33 exhibit $I_{50}$ values against *B. fragilis* CfiA metallo-β-lactamase <500 μM. $I_{50}$ values for compounds E2, E20 and E26 were found to be <1 μM. Compounds of Examples 19, 21, 27 and captopril (N-(3'-mercapto-2'(S)-methylpropionyl)-L-proline) exhibit weak but significant activity against *Xanthomonas maltophilia* L-1 and *Bacillus cereus* II metallo-β-lactamases. Antibacterial activity of compounds of the invention in combination with carbapenem antibiotics against strains of *Bacteroides fragllis* which produce metallo-β-lactamase: [MIC =minimum inhibitory concentration (μg/ml)]

Antibacterial activity of the carbapenems was potentiated as follows:

TABLE 1

Compound E20 in combination with meropenem:

| Strain | metallo-β-lactamase | MIC (μg/ml) alone Compound E20 | MIC (μg/ml) alone Meropenem | MIC of meropenem in the presence of these concentrations (μg/ml) of compound E20 | | | | |
|---|---|---|---|---|---|---|---|---|
| | | | | 64 | 32 | 16 | 8 | 4 |
| *B. fragilis* 460 | CfiA | >512 | 128 | 2 | 4 | 8 | 16 | 32 |
| *B. fragilis* 262 | CfiA | >512 | 128 | 2 | 4 | 4 | 8 | 16 |

TABLE 2

Compound E20 in combination with imipenem:

| Strain | metallo-β-lactamase | MIC (μg/ml) alone Compound E20 | MIC (μg/ml) alone Imipenem | MIC of imipenem in the presence of these concentrations (μg/ml) of compound E2 | | | | |
|---|---|---|---|---|---|---|---|---|
| | | | | 64 | 32 | 16 | 8 | 4 |
| *B. fragilis* 460 | CfiA | >512 | 16 | 0.5 | 1 | 1 | 2 | 4 |
| *B. fragilis* 262 | CfiA | >512 | 4 | 0.5 | 0.5 | 0.5 | 2 | 4 |

We claim:

1. A method of treatment of bacterial infections in humans or animals which comprises administering, in combination with a β-lactam antibiotic, a therapeutically effective amount of a compound of formula (I) or a pharmaceutically acceptable salt, or solvate thereof:

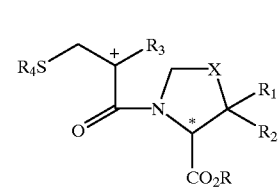

wherein:

X is S, $S(O)_n$ or $CH_2$;

n is 1 or 2

R is hydrogen; a salt forming cation; an ester-forming group which is formulae (i), (ii), (iii), (iv) or (v):

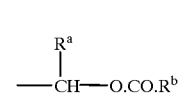

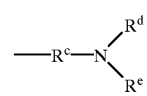

-continued

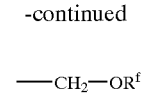

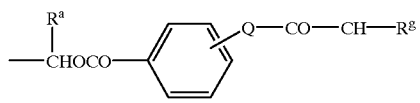

(IV)

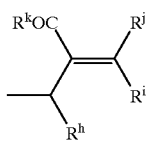

(V)

wherein $R^a$ is hydrogen, $(C_{1-6})$ alkyl, $(C_{3-7})$ cycloalkyl, methyl, or phenyl; $R^b$ is $(C_{1-6})$alkyl, $(C_{1-6})$ alkoxy, phenyl, benzyl, $(C_{3-7})$ cycloalkyl, $(C_{3-7})$ cycloalkyloxy, $(C_{1-6})$ alkyl$(C_{3-7})$ cycloalkyl, 1-amino $(C_{1-6})$ akyl, or 1-$(C_{1-6}$ alkyl)amino $(C_{1-6})$ alkyl; or $R^a$ and $R^b$ together form a 1,2-phenylene group unsubstituted or substituted by one or two methoxy groups; $R^c$ is $(C_{1-6})$ alkylene unsubstituted or substituted with a methyl or ethyl group and $R^d$ and $R^e$ independently represent $(C_{1-6})$ alkyl; $R^f$ represents $(C_{1-6})$ alkyl; $R^g$ is hydrogen or phenyl unsubstituted or substituted by up to three groups selected from halogen, $(C_{1-6})$ alkyl, or $(C_{1-6})$ alkoxy; O is oxygen or NH; $R^h$ is hydrogen or $(C_{1-6})$ alkyl; $R^i$ is hydrogen, $(C_{1-6})$alkyl unsubstituted or substituted by halogen, $(C_{2-6})$ alkenyl, $(C_{1-6})$ alkoxycarbonyl, aryl or heteroaryl: or $R^h$ and $R^i$ together form $(C_{1-6})$ alkylene; $R^j$ is hydrogen. $(C_{1-6})$ alkyl or $(C_{1-6})$ alkoxycarbonyl; and $R^k$ is $(C_{1-8})$alkyl, $(C_{1-8})$ alkoxy, $(C_{1-6})$ alkoxy$(C_{1-6})$alkoxy or aryl;

or an ester-forming group which is

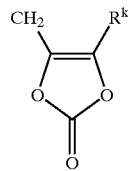

wherein $R^k$ is hydrogen, $C_{1-6}$ alkyl or phenyl:

$R_1$ and $R_2$ are each independently hydrogen, $(C_{1-10})$alkyl, aryl, heterocyclyl or substituted $(C_{1-10})$alkyl, wherein any substituent is aryl, heterocyclyl, hydroxy, $(C_{1-6})$ alkoxy, $(C_{1-6})$alkanoyloxy, halogen, mercapto, $(C_{1-6})$ alkylthio, heterocyclylthio, amino, (mono or di)-$(C_{1-6})$ alkylamino, $(C_{1-6})$alkanoylamino, carboxy, or $(C_{1-6})$ alkoxycarbonyl;

$R_3$ is hydrogen, $(C_{1-6})$alkyl unsubstituted or substituted by up to three halogen atoms, $(C_{2-6})$alkenyl, $(C_{2-6})$ alkynyl, aryl, aryl$(C_{1-6})$alkyl, heterocyclyl or heterocyclyl$(C_{1-6})$alkyl; and $R_4$ is hydrogen, lower alkylcarbonyl, substituted or unsubstituted benzoyl, or substituted or unsubstituted phenyl lower alkyl carbonyl.

2. The method according to claim 1 using a compound of formula (I) which is

3-[S-acetyl-2'(RS)-benzyl-3'-mercaptopropionyl]-4(S)-carboxy-5,5-dimethylthiazolidine;

3-[2'(RS)-benzyl-3'-mercaptopropionyl]-4(S)-carboxy-5,5-dimethylthiazolidine;

N-[S-Acetyl-3'-mercapto-2'(RS)-methylpropionyl]-D-proline;

N-[3'-Mercapto-2'(RS)-methylpropionyl]-D-proline;

N-(S-Acetyl-3'-mercapto-2'(S)-methylpropionyl)-D-proline;

N-(3'-mercapto-2'(S)-methylpropionyl)-D-proline;

3-[S-Acetyl-3'-mercaptopropionyl]-4(S)-carboxy-5,5-dimethylthiazolidine;

3-[3'-Mercaptopropionyl]-4(S)-carboxy-5,5-dimethylthiazolidine;

3-[S-Acetyl-3'-mercapto-2'(S)-methylpropionyl]-4(S)-carboxy-5,5-dimethylthiazolidine;

3-[3'-Mercapto-2'(S)-methylpropionyl]-4(S)-carboxy-5,5-dimethylthiazolidine;

3-[S-Acetyl-2'(RS)-benzyl-3'-mercaptopropionyl]-4(R)-carboxy-5,5-dimethylthiazolidine;

3-[2'(RS)-benzyl-3'-mercaptopropionyl]-4(R)-carboxy-5,5-dirmethylthiazolidine;

3-[S-Acetyl-3'-mercapto-2'(RS)-methylpropionyl]-4(S)-carboxy-5,5-dimethylthiazolidine;

3-[3'-Mercapto-2'(RS)-methylpropionyl]-4(S)-carboxy-5,5-dimethylthiazolidine;

N-[S-Acetyl-2'(RS)-benzyl-3'-mercaptopropionyl]-D-proline;

N-[2'(RS)-benzyl-3'-mercaptopropionyl]-D-proline;

3-[S-Acetyl-2'(RS)-benzyl-3'-mercaptopropionyl]-4(S)-carboxythiazolidine;

3-[2(RS)-benzyl-3'-mercaptopropionyl]-4(S)-carboxythiazolidine;

3-[2'(R)-benzyl-3'-mercaptopropionyl]-4(S)-carboxy-5,5-dimethylthiazolidine;

3-[2'(S)-benzyl-3'-mercaptopropionyl]-4(S)-carboxy-5,5-dimethylthiazolidine;

3-[3'-Mercapto-2'(R)-methylpropionyl]-4(S)-carboxy-5,5-dimethylthiazolidine;

3-[S-Acetyl-3'-mercapto-2'(S)-methylpropionyl]-4(R)-carboxy-5,5-dimethylthiazolidine;

3-[Mercapto-2'(S)-methylpropionyl]-4(R)-carboxy-5,5-dimethylthiazolidine;

N-[S-Acetyl-2'(RS)-benzyl-3'-mercaptopropionyl]-L-proline;

N-[2'(RS)-benzyl-3'-mercaptopropionyl]-L-proline;

3-[2'(S)-benzyl-3'-mercaptopropionyl]-4(S)-carboxy-5,5-dimethylthiazolidine- 1-oxide; (sulphoxide isomer A)

3-[2'(S)-benzyl-3'-mercaptopropionyl]-4(S)-carboxy-5,5-dimethylthiazolidine- 1-oxide (sulphoxide isomer B);

3-[2'(S)-benzyl-3'-mercaptopropionyl]-4(R)-carboxy-5,5-dimethylthiazolidine;

3-[2'(R)-benzyl-3'-mercaptopropionyl]-4(R)-carboxy-5,5-dimethylthiazolidine;

3-[2'(R or S)-benzyl-3'-mercaptopropionyl]-4(S)-carboxythiazolidine;

3-[2'(S or R)-benzyl-3'-mercaptopropionyl]-4(S)-carboxythiazolidine;

3-[2'(RS)-mercaptomethyl4'-phenylbutanoyl]-4(S)-carboxy-5,5-dimethylthiazolidine; or 3-[2'(RS)-mercaptomethyl-5'-phenylpentanoyl]-4(S)-carboxythiazolidine.

3. The composition of claim 2 wherein the β-lactam antibiotic is a carbapenem selected from the group consisting of imipenem, meropenem, biapenem, BMS181139 ([4 R-[4alpha,5beta,6beta(R*)]]-4-[2-[(aminoiminomethyl)amino]ethyl]-3-[(2-cyanoethyl)thio]-6-(1-hydroxyethyl)-7-oxo-1-azabicyclo[3.2.0]hept-2-ene-2-carboxylic acid), BO2727 ([4 R-3[3 S*,5 S*(R*)],4alpha,5beta,6beta(R*)]]-6-(1-hydroxyethyl)-3-[[5-[1-hydroxy-3-(methylamino) propyl]-3-pyrrolidinyl]thio]-4-methyl-7-oxo-1-azabicyclo [3.2.0] hept-2-ene-2-carboxylic acid monohydrochloride), ER35786 ((1 R, 5 S, 6 S)-6-[1(R)-Hydroxymethyl]-2-[2(S)-[1(R)-hydroxy-1-[pyrrolidin-3(R)-yl] methyl]pyrrolidin-4 (S)-ylsulfanyl]-1-methyl-1-carba-2-penem-3-carboxylic acid hydrochloride), and S4661 ((1 R,5 S,6 S)-2-[(3 S,5 S)-5-(sulfamoylaminomethyl) pyrrolidin-3-yl]thio-6-[(1 R)-1-hydroxyethyl]-1-methylcarbapen-2-em-3-carboxylic acid).

* * * * *